United States Patent [19]
Blenke et al.

[11] Patent Number: 6,022,431
[45] Date of Patent: Feb. 8, 2000

[54] METHOD OF MAKING PREFASTENED ABSORBENT ARTICLES HAVING A STRETCH BAND

[75] Inventors: Timothy James Blenke, Neenah; Patrick Sean McNichols, Hortonville; Robert Eugene Vogt, Neenah, all of Wis.

[73] Assignee: Kimberly-Clark Worldwide, Inc., Neenah, Wis.

[21] Appl. No.: 09/100,547

[22] Filed: Jun. 19, 1998

[51] Int. Cl.[7] .............................. A61F 13/56; A61F 13/15
[52] U.S. Cl. .......................... 156/73.1; 156/85; 156/164; 156/227; 156/229; 156/264
[58] Field of Search ..................... 156/163, 164, 156/229, 227, 226, 264, 85, 73.1, 297

[56] References Cited

U.S. PATENT DOCUMENTS

| | | |
|---|---|---|
| H1558 | 7/1996 | Goulait et al. . |
| H1674 | 8/1997 | Ames et al. . |
| D. 290,780 | 7/1987 | Wistrand . |
| D. 389,320 | 1/1998 | Vinnage et al. . |
| 1,079,479 | 11/1913 | Earnshaw . |
| 1,485,001 | 2/1924 | Wills . |
| 1,657,909 | 1/1928 | Abramovich . |
| 1,705,194 | 3/1929 | Marinsky . |

(List continued on next page.)

FOREIGN PATENT DOCUMENTS

| | | |
|---|---|---|
| 667899 | 4/1996 | Australia . |
| 2096672 | 11/1993 | Canada . |
| 2103992 A1 | 2/1994 | Canada . |
| 2187021 A1 | 10/1995 | Canada . |
| 2187366 A1 | 10/1995 | Canada . |
| 0 206 208 B1 | 12/1986 | European Pat. Off. . |
| 0 217 032 A2 | 4/1987 | European Pat. Off. . |
| 0 251 251 A3 | 1/1988 | European Pat. Off. . |
| 0 463 276 A1 | 1/1992 | European Pat. Off. . |

(List continued on next page.)

OTHER PUBLICATIONS

Derwent World Patent Database abstract of FR 2762507 A1: Description of RAHALA, "Baby's Disposable Nappy."
Derwent World Patent Database abstract of JP 6–063076 A: Description of Kao Corp. (Kaos), "Throw Away Diaper Or Nappy."
Derwent World Patent Database abstract of JP 95–044941 B2: Description of ZUIKO KK (ZUIK–N), "Simple Solid Diaper For Eliminating Waste of Material by Using Square Shape."
Derwent World Patent Database abstract of JP 9–276334 A: Description of Kao Corp. (Kaos), "Disposable Baby Nappy."
Derwent World Patent Database abstract of JP 11–070143 A: Description of TOYO EISAI KK (TOEI–N), "Disposable Diaper For Adults And Children."
Derwent World Patent Database abstract of JP 11–076299 A: Description of UNI–CHARM KK (UNIC–N), "Disposable Diaper."

*Primary Examiner*—Jeff H. Aftergut
*Attorney, Agent, or Firm*—Jeffrey B. Curtin

[57] ABSTRACT

Disposable absorbent articles which include an outer cover, an absorbent chassis and a stretch band and methods of making the same are described. The stretch band is incorporated into the article by providing a waist panel which includes a pair of primary fasteners attached to a first surface on opposed side margins of the waist panel. The stretch band is attached to the second surface of the waist panel. The stretch band includes a pair of secondary fasteners on opposite end portions of the stretch band which are releasably engaged with the second surface of the waist panel. The second surface of the waist panel may then be attached to an inner surface of the outer cover such that the stretch band is slidably contained between the outer cover and the waist panel. The primary fasteners on the waist panel and the secondary fasteners on the stretch band are configured to releasably engage an opposite waist region of the absorbent article to initially fasten the absorbent article on the wearer and further conform the waist regions to the wearer's body after the absorbent article has been initially placed on the wearer.

8 Claims, 5 Drawing Sheets

U.S. PATENT DOCUMENTS

| | | |
|---|---|---|
| 1,762,468 | 6/1930 | Brewer . |
| 1,963,334 | 6/1934 | Neilson . |
| 2,201,255 | 5/1940 | Wilson, Jr. . |
| 2,242,977 | 5/1941 | Marcos . |
| 2,475,175 | 7/1949 | Cadous . |
| 2,477,914 | 8/1949 | Webb . |
| 2,545,761 | 3/1951 | Brink . |
| 2,570,963 | 10/1951 | Mesmer . |
| 2,630,120 | 3/1953 | Nielson . |
| 2,743,725 | 5/1956 | Matthews . |
| 2,801,632 | 8/1957 | Burner et al. . |
| 2,808,831 | 10/1957 | Winslett . |
| 2,830,589 | 4/1958 | Doner . |
| 2,833,282 | 5/1958 | Moore . |
| 2,910,982 | 11/1959 | Woodward . |
| 2,931,361 | 4/1960 | Sostrin . |
| 3,039,466 | 6/1962 | Wilson . |
| 3,077,193 | 2/1963 | Mann . |
| 3,610,244 | 10/1971 | Jones, Sr. . |
| 3,638,651 | 2/1972 | Torr . |
| 3,653,381 | 4/1972 | Warnken . |
| 3,825,006 | 7/1974 | Ralph . |
| 3,882,871 | 5/1975 | Taniguchi . |
| 4,024,867 | 5/1977 | Mesek . |
| 4,051,853 | 10/1977 | Egan, Jr. . |
| 4,051,854 | 10/1977 | Aaron . |
| 4,066,081 | 1/1978 | Schaar . |
| 4,074,716 | 2/1978 | Schaar . |
| 4,089,068 | 5/1978 | Swallow . |
| 4,090,516 | 5/1978 | Schaar . |
| 4,205,679 | 6/1980 | Repke et al. . |
| 4,210,143 | 7/1980 | De Jonckheere . |
| 4,337,771 | 7/1982 | Pieniak et al. . |
| 4,410,327 | 10/1983 | Baggaley . |
| 4,500,316 | 2/1985 | Damico . |
| 4,515,595 | 5/1985 | Kievit et al. . |
| 4,522,853 | 6/1985 | Szonn et al. . |
| 4,525,407 | 6/1985 | Ness . |
| 4,563,185 | 1/1986 | Reiter . |
| 4,568,341 | 2/1986 | Mitchell et al. . |
| 4,581,772 | 4/1986 | Smith . |
| 4,596,055 | 6/1986 | Aach et al. . |
| 4,598,528 | 7/1986 | McFarland et al. . |
| 4,604,096 | 8/1986 | Dean et al. . |
| 4,610,680 | 9/1986 | LaFleur . |
| 4,610,681 | 9/1986 | Strohbeen et al. . |
| 4,615,695 | 10/1986 | Cooper . |
| 4,617,022 | 10/1986 | Pigneul et al. . |
| 4,619,649 | 10/1986 | Roberts . |
| 4,623,339 | 11/1986 | Ciraldo et al. . |
| 4,630,320 | 12/1986 | Van Gompel . |
| 4,663,220 | 5/1987 | Wisneski et al. . |
| 4,675,918 | 6/1987 | O'Brien . |
| 4,699,622 | 10/1987 | Toussant et al. . |
| 4,704,116 | 11/1987 | Enloe . |
| 4,726,874 | 2/1988 | Van Vliet . |
| 4,728,326 | 3/1988 | Gilles . |
| 4,743,239 | 5/1988 | Cole . |
| 4,747,846 | 5/1988 | Boland et al. . |
| 4,753,646 | 6/1988 | Enloe . |
| 4,753,650 | 6/1988 | Williams . |
| 4,798,603 | 1/1989 | Meyer et al. . |
| 4,801,485 | 1/1989 | Sallee et al. . |
| 4,808,252 | 2/1989 | Lash . |
| 4,826,499 | 5/1989 | Ahr . |
| 4,850,988 | 7/1989 | Aledo et al. . |
| 4,850,992 | 7/1989 | Amaral et al. . |
| 4,857,067 | 8/1989 | Wood et al. . |
| 4,883,481 | 11/1989 | Blanchard . |
| 4,892,598 | 1/1990 | Stevens et al. . |
| 4,904,252 | 2/1990 | Fitzgerald . |
| 4,909,802 | 3/1990 | Ahr et al. . |
| 4,911,702 | 3/1990 | O'Leary et al. . |
| 4,917,682 | 4/1990 | Lancaster et al. . |
| 4,936,840 | 6/1990 | Proxmire . |
| 4,937,887 | 7/1990 | Schreiner . |
| 4,938,753 | 7/1990 | Van Gompel et al. . |
| 4,944,733 | 7/1990 | Casale . |
| 4,961,736 | 10/1990 | McCloud . |
| 4,988,346 | 1/1991 | Pfefferkorn . |
| 4,998,929 | 3/1991 | Bjorksund et al. . |
| 5,019,072 | 5/1991 | Polski . |
| 5,019,073 | 5/1991 | Roessler et al. . |
| 5,040,244 | 8/1991 | Tubbs . |
| 5,062,839 | 11/1991 | Anderson . |
| 5,066,289 | 11/1991 | Polski . |
| 5,069,678 | 12/1991 | Yamamoto et al. . |
| 5,074,854 | 12/1991 | Davis . |
| 5,087,253 | 2/1992 | Cooper . |
| 5,106,382 | 4/1992 | Henry . |
| 5,106,385 | 4/1992 | Allen et al. . |
| 5,110,403 | 5/1992 | Ehlert . |
| 5,112,326 | 5/1992 | Quadrini . |
| 5,135,522 | 8/1992 | Fahrenkrug et al. . |
| 5,140,757 | 8/1992 | Terada . |
| 5,163,932 | 11/1992 | Nomura et al. . |
| 5,170,505 | 12/1992 | Rohrer . |
| 5,176,668 | 1/1993 | Bernardin . |
| 5,176,670 | 1/1993 | Roessler et al. . |
| 5,176,672 | 1/1993 | Bruemmer et al. . |
| 5,185,011 | 2/1993 | Strasser . |
| 5,186,779 | 2/1993 | Tubbs . |
| 5,187,817 | 2/1993 | Zolner . |
| 5,192,606 | 3/1993 | Proxmire et al. . |
| 5,226,992 | 7/1993 | Morman . |
| 5,242,436 | 9/1993 | Weil et al. . |
| 5,275,590 | 1/1994 | Huffman et al. . |
| 5,304,162 | 4/1994 | Kuen . |
| 5,340,431 | 8/1994 | Terada . |
| 5,358,500 | 10/1994 | Lavon et al. . |
| 5,368,584 | 11/1994 | Clear et al. . |
| 5,368,585 | 11/1994 | Dokken . |
| 5,370,632 | 12/1994 | Beplate . |
| 5,370,634 | 12/1994 | Ando et al. . |
| 5,373,587 | 12/1994 | Sexton . |
| 5,374,262 | 12/1994 | Keuhn, Jr. et al. . |
| 5,383,872 | 1/1995 | Roessler et al. . |
| 5,386,595 | 2/1995 | Kuen et al. . |
| 5,397,639 | 3/1995 | Tollini . |
| 5,399,219 | 3/1995 | Roessler et al. . |
| 5,401,275 | 3/1995 | Flug et al. . |
| 5,423,789 | 6/1995 | Kuen . |
| 5,445,628 | 8/1995 | Gipson et al. . |
| 5,451,219 | 9/1995 | Suzuki et al. . |
| 5,462,541 | 10/1995 | Bruemmer et ala. . |
| 5,489,282 | 2/1996 | Zehner et al. . |
| 5,499,978 | 3/1996 | Buell et al. . |
| 5,500,063 | 3/1996 | Jessup . |
| 5,509,915 | 4/1996 | Hanson et al. . |
| 5,527,302 | 6/1996 | Endres et al. . |
| 5,531,731 | 7/1996 | Brusky . |
| 5,531,732 | 7/1996 | Wood . |
| 5,537,722 | 7/1996 | Niederhofer et al. . |
| 5,540,796 | 7/1996 | Fries . |
| 5,545,158 | 8/1996 | Jessup . |
| 5,545,275 | 8/1996 | Herrin et al. . |
| 5,554,146 | 9/1996 | Niederhofer et al. . |
| 5,562,650 | 10/1996 | Everett et al. . |
| 5,569,232 | 10/1996 | Roe et al. . |
| 5,569,234 | 10/1996 | Buell et al. . |
| 5,571,586 | 11/1996 | Gobran . |
| 5,575,784 | 11/1996 | Ames-Ooten et al. . |

| | | |
|---|---|---|
| 5,582,606 | 12/1996 | Bruemmer et al. . |
| 5,591,152 | 1/1997 | Buell et al. . |
| 5,593,401 | 1/1997 | Sosalla et al. . |
| 5,601,546 | 2/1997 | Tanji et al. . |
| 5,607,416 | 3/1997 | Yamamoto et al. . |
| 5,611,789 | 3/1997 | Seth . |
| 5,618,366 | 4/1997 | Suekane . |
| 5,624,420 | 4/1997 | Bridges et al. . |
| 5,624,424 | 4/1997 | Saisaka et al. . |
| 5,624,428 | 4/1997 | Sauer . |
| 5,624,429 | 4/1997 | Long et al. . |
| 5,626,574 | 5/1997 | Sasaki et al. . |
| 5,628,738 | 5/1997 | Suekane . |
| 5,629,063 | 5/1997 | Gobran . |
| 5,634,916 | 6/1997 | Lavon et al. . |
| 5,656,111 | 8/1997 | Dilnik et al. . |
| 5,662,637 | 9/1997 | Kitaoka et al. . |
| 5,662,638 | 9/1997 | Johnson et al. . |
| 5,665,084 | 9/1997 | Richmond . |
| 5,669,897 | 9/1997 | Lavon et al. . |
| 5,685,874 | 11/1997 | Buell et al. . |
| 5,690,626 | 11/1997 | Suzuki et al. . |
| 5,690,627 | 11/1997 | Clear et al. . |
| 5,693,038 | 12/1997 | Suzuki et al. . |
| 5,707,364 | 1/1998 | Coates . |
| 5,711,832 | 1/1998 | Glaug et al. . |
| 5,759,317 | 6/1998 | Justmann . |
| 5,772,825 | 6/1998 | Schmitz . |
| 5,788,685 | 8/1998 | Ronnberg et al. . |
| 5,788,797 | 8/1998 | Herrin et al. . |
| 5,795,433 | 8/1998 | Niedermeyer et al. ............. 156/227 X |
| 5,827,259 | 10/1998 | Laux et al. . |
| 5,827,260 | 10/1998 | Suzuki et al. . |
| 5,830,206 | 11/1998 | Larsson . |
| 5,855,574 | 1/1999 | Kline et al. . |
| 5,876,531 | 3/1999 | Jacobs et al. . |
| 5,897,545 | 4/1999 | Kline et al. . |
| 5,904,802 | 5/1999 | Niedermeyer et al. ............. 156/227 X |
| 5,919,334 | 7/1999 | Niedermeyer et al. ............. 156/227 X |
| B1 4,315,508 | 11/1988 | Bolick . |
| B1 4,964,860 | 1/1994 | Gipson et al. . |

FOREIGN PATENT DOCUMENTS

| | | |
|---|---|---|
| 0 532 034 A2 | 3/1993 | European Pat. Off. . |
| 0 544 703 B1 | 6/1993 | European Pat. Off. . |
| 0 696 911 B1 | 2/1996 | European Pat. Off. . |
| 0 753 292 A2 | 1/1997 | European Pat. Off. . |
| 0 487 758 B1 | 3/1997 | European Pat. Off. . |
| 0 809 992 A1 | 12/1997 | European Pat. Off. . |
| 0 878 180 A2 | 11/1998 | European Pat. Off. . |
| 6-77718 U | 11/1994 | Japan . |
| 7-213553 | 8/1995 | Japan . |
| 7-227407 | 8/1995 | Japan . |
| 7-255773 | 10/1995 | Japan . |
| 7-299094 | 11/1995 | Japan . |
| 8-229072 | 9/1996 | Japan . |
| 9-287 U | 5/1997 | Japan . |
| 11-47188 | 2/1999 | Japan . |
| 1 520 740 | 8/1978 | United Kingdom . |
| 2 244 422 | 12/1991 | United Kingdom . |
| 2 267 024 | 11/1993 | United Kingdom . |
| 2 288 314 | 10/1995 | United Kingdom . |
| 2 288 315 | 10/1995 | United Kingdom . |
| 2 288 316 | 10/1995 | United Kingdom . |
| 0 291 783 | 2/1996 | United Kingdom . |
| 2 294 867 | 5/1996 | United Kingdom . |
| 2 297 473 | 6/1996 | United Kingdom . |
| WO 83/04163 A1 | 12/1983 | WIPO . |
| WO 90/07313 A1 | 7/1990 | WIPO . |
| WO 91/04724 A1 | 4/1991 | WIPO . |
| WO 91/08725 A1 | 6/1991 | WIPO . |
| WO 92/22274 A1 | 12/1992 | WIPO . |
| WO 93/09742 A1 | 5/1993 | WIPO . |
| WO 94/17768 A1 | 8/1994 | WIPO . |
| WO 95/01148 A1 | 1/1995 | WIPO . |
| WO 95/02383 A1 | 1/1995 | WIPO . |
| WO 95/13772 A1 | 5/1995 | WIPO . |
| WO 95/22951 A1 | 8/1995 | WIPO . |
| WO 95/27460 A1 | 10/1995 | WIPO . |
| WO 95/27462 A1 | 10/1995 | WIPO . |
| WO 95/29657 A1 | 11/1995 | WIPO . |
| WO 96/03101 A1 | 2/1996 | WIPO . |
| WO 96/18315 A1 | 10/1996 | WIPO . |
| WO 96/32084 A1 | 10/1996 | WIPO . |
| WO 97/15260 A1 | 5/1997 | WIPO . |
| WO 97/23186 A1 | 7/1997 | WIPO . |
| WO 97/25951 A1 | 7/1997 | WIPO . |
| WO 97/31605 A1 | 9/1997 | WIPO . |
| WO 97/32555 A1 | 9/1997 | WIPO . |
| WO 97/33547 A1 | 9/1997 | WIPO . |
| WO 97/46197 A1 | 12/1997 | WIPO . |
| WO 98/03140 A1 | 1/1998 | WIPO . |
| WO 98/18421 A1 | 5/1998 | WIPO . |
| WO 98/56328 A1 | 12/1998 | WIPO . |
| WO 99/07319 A1 | 2/1999 | WIPO . |

METHOD OF MAKING PREFASTENED ABSORBENT ARTICLES HAVING A STRETCH BAND

FIELD OF THE INVENTION

The present invention relates to disposable absorbent articles which are adapted to contain body exudates. More particularly, the present invention relates to absorbent articles having stretch bands and methods of making the same.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the care giver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. For example, such absorbent articles can assist in the toilet training of children.

Conventional diapers have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost corners of the diaper in the back waist region of the diaper and a complimentary fastener, such as a taping panel, located on the outer surface of the outer cover of the diaper in the front waist portion of the diaper. In such a configuration, the diaper has been positioned between the legs of the wearer and the adhesive tape tabs have been releasably attached to the taping panel to secure the back waist portion to the front waist portion of the diaper to secure the diaper about the waist of the wearer. Such conventional diapers can be easy to fasten about and remove from the wearer after use without undesirably soiling the care giver.

However, such conventional diapers generally have one set of fasteners which must be disengaged and reattached to further conform the waist portions of the diaper to the wearer if the appropriate fit is not obtained upon the first fastening. Such disengagement and reattachment can be difficult to accomplish when the wearer is active. Moreover, such conventional diapers are not provided in a prefastened configuration and thus are not configured to be pulled up or down over the hips of the wearer when the fasteners are attached.

Several attempts have been made to provide absorbent articles which fit the waist of the wearer to effectively contain body exudates, are capable of being pulled up or down over the hips of the wearer and provide ease of cleaning and removal after being soiled. For example, some conventional absorbent articles have included more than one pair of fasteners to provide improved securement of the article about the waist of the wearer. Moreover, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be torn to remove the training pant from the wearer after it has been soiled.

However, many of such attempts have not been completely satisfactory. For example, absorbent articles which have had more than one pair of fasteners have not always provided conformance of the waist portions of the article to the complete waist of the wearer. Instead, many of such articles have been designed to conform only one of the waist regions or only the hip regions to the waist of the wearer which may still result in gaps between the article and the waist of the wearer in the other waist portions. Moreover, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. As a result, many of such articles have not contained bodily exudates as effectively as conventional diaper-type articles which can be adjusted to achieve a more conforming fit to the wearer. Further, the removal of soiled absorbent articles which have integral side panels, such as conventional training pants, has not been completely satisfactory. For example, the side panels have been difficult to tear when attempting to remove the article from the waist of the wearer instead of pulling the article down over the hips of the wearer.

Accordingly, despite the attempts to develop improved absorbent articles, there remains a need for absorbent articles which can provide conformance completely around the waist of the wearer and the benefits of both conventional training pants and conventional diapers. That is, there remains a need for absorbent articles which conform to the wearer to effectively contain bodily exudates, which are capable of being pulled up and down over the hips and buttocks of the wearer without opening, and which are readily secured about and removed from the wearer in a convenient and clean manner. Moreover, there is a need for improved methods of reliably and consistently making such absorbent articles.

SUMMARY OF THE INVENTION

In response to the difficulties and problems discussed above, a new disposable absorbent article which includes a stretch band fastening system and methods of making the same have been discovered. In one aspect, the present invention concerns a method of continuously making stretch band assemblies for use on disposable absorbent articles. The method includes providing two continuous, laterally spaced apart ribbons of fastener material; attaching stretch bands between and to the ribbons of fastener material at longitudinally spaced apart locations in a continuous ladder type configuration; and selectively cutting the continuous web of stretch band assemblies into discrete stretch band assemblies. Each of the stretch band assemblies defines one of the stretch bands and a pair of laterally spaced apart fasteners attached to opposite end portions of the stretch band. Each of the discrete stretch band assemblies is configured to be attached to one of the absorbent articles such that the stretch band is slidably contained in the absorbent article.

In another aspect, the present invention concerns a method of making a disposable absorbent article which includes an outer cover and an absorbent chassis. The method includes the steps of:

a) providing a waist panel which includes a pair of primary fasteners attached on the opposed side margins of the waist panel;
b) attaching a stretch band which includes a pair of secondary fasteners on opposite end portions thereof to the waist panel;
c) attaching the waist panel to an inner surface of the outer cover in one waist region of the absorbent article such that the stretch band is slidably contained between the outer cover and the waist panel; and
d) attaching the absorbent chassis to the outer cover to provide the disposable absorbent article. The secondary fasteners on the stretch band are configured to releasably engage an opposite waist region of the absorbent article to further conform the waist regions to a wearer's body after the absorbent article has been placed on the wearer.

The disposable absorbent article may also be provided in a prefastened configuration by folding the article about a fold line extending in a lateral direction through the crotch region of the article thereby positioning the waist regions of the absorbent article in a facing relationship and releasably engaging the primary fasteners with an outer surface of the absorbent article in the opposite waist region of the absorbent article. In such a configuration, the secondary fasteners on the stretch band are configured to releasably engage the opposite waist region to conform the waist regions to a wearer's body after the prefastened absorbent article is pulled on over a wearer's hips.

In a particular embodiment, the waist panel is provided by providing a continuous web of material; attaching a ribbon of primary fastener material along a longitudinal length of the web of material; cutting the continuous web of material and ribbon along the longitudinal length in a serpentine path to provide two continuous sections of material each defining a straight edge and a serpentine cut edge which includes primary fasteners attached thereto; crossing the sections of material over one another to position the serpentine cut edge of each of the sections of material laterally outward from the straight edge and to position the straight edges in an overlapping configuration; securing the straight edges together to provide a continuous web of waist panel material; and cutting the continuous web of waist panel material at spaced apart locations to provide the individual waist panel.

In another particular embodiment, the stretch band is provided by providing two continuous, laterally spaced apart ribbons of secondary fastener material; attaching band segments between and to the ribbons of fastener material at longitudinally spaced apart locations in a continuous ladder type configuration to provide a continuous web of stretch band material; and selectively cutting the continuous web of stretch band material to provide the stretch band. The two continuous ribbons of secondary fastener material may be provided by a continuous web of secondary fastener material which is cut along a longitudinal length in a serpentine path to provide the two ribbons of secondary fastener material each defining a serpentine cut edge and an opposite edge and crossing the ribbons over one another to position the serpentine cut edge of each of the ribbons laterally outward from the opposite edge of the respective ribbon before attaching the band segments thereto.

In yet another aspect, the present invention concerns a disposable absorbent article which defines an absorbent, a front waist region, a back waist region, a crotch region which extends between and connects the waist regions, a lateral direction and a longitudinal direction. The absorbent article includes an outer cover, a waist panel located in a facing relationship with the outer cover in one of the waist regions and a stretch band which is slidably located between the waist panel and the outer cover. The stretch band includes a pair of fasteners on the opposed end portions of the stretch band which are configured to releasably engage an outer surface of the opposite waist region of the article to conform the waist regions to a wearer's body.

In still another aspect, the present invention concerns a disposable absorbent article which defines an absorbent, a front waist region, a back waist region, a crotch region which extends between and connects the waist regions, a lateral direction and a longitudinal direction. The absorbent article includes an outer cover and a waist panel which is connected to the outer cover in the back waist region of the absorbent article. The waist panel also defines opposed side margins which extend laterally outward beyond the outer cover. The article also includes a pair of primary fasteners which are located on a first surface on the opposed side margins of the waist panel and which are configured to releasably engage an outer surface of the absorbent article in the front waist region. The article further includes a stretch band which is slidably located between the waist panel and the outer cover. The stretch band includes a pair of secondary fasteners located on the opposed end portions of the stretch band. The secondary fasteners are configured to releasably engage the outer surface of the front waist region to further conform the waist regions to a wearer's body after the primary fasteners are releasably engaged.

The present invention advantageously provides disposable absorbent articles which include a stretch band for improved fit and performance and methods of making the same. In particular, the present invention provides a method of attaching a stretch band to a disposable absorbent article in a reliable and consistent manner.

The absorbent article of the present invention may further be capable of being reliably pulled up or down over the hips of the wearer to assist in the toilet training of the wearer similar to conventional training pants. After being pulled up over the hips of the wearer, the stretch band of the absorbent article can be used to further conform the waist of the article to the wearer's body for improved fit and leakage control. Moreover, similar to conventional diapers, the absorbent article of the present invention can advantageously be applied to and removed from the wearer after it has been soiled with relative ease and cleanliness.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns disposable absorbent articles which are configured to closely conform to the body of the wearer to effectively contain body exudates and methods of making the same. The absorbent articles may be provided in a prefastened configuration such that they can be pulled up or down over the hips and buttocks of the wearer and are configured to be easily secured to and removed directly from the waist of the wearer. As such, the absorbent articles of the present invention can function in a similar manner to conventional training pants when left in the prefastened configuration or in a similar manner to conventional diapers when in an unfastened configuration. The disposable absorbent articles are adapted to be worn adjacent to the body of a wearer to absorb and contain various exudates discharged from the body. As used herein, the term "disposable" refers to articles which are intended to be discarded after a limited use and which are not intended to be laundered or otherwise restored for reuse.

The disposable absorbent articles of the present invention and the methods of making the same will be described in terms of a disposable diaper article which is adapted to be worn by infants about the lower torso. In particular, the absorbent articles will be described in terms of a disposable absorbent diaper having a stretch band. It is understood that the articles and methods of the present invention are equally adaptable for other types of absorbent articles such as adult incontinent products, training pants, feminine hygiene products, other personal care or health care garments, and the like.

Figure 1:
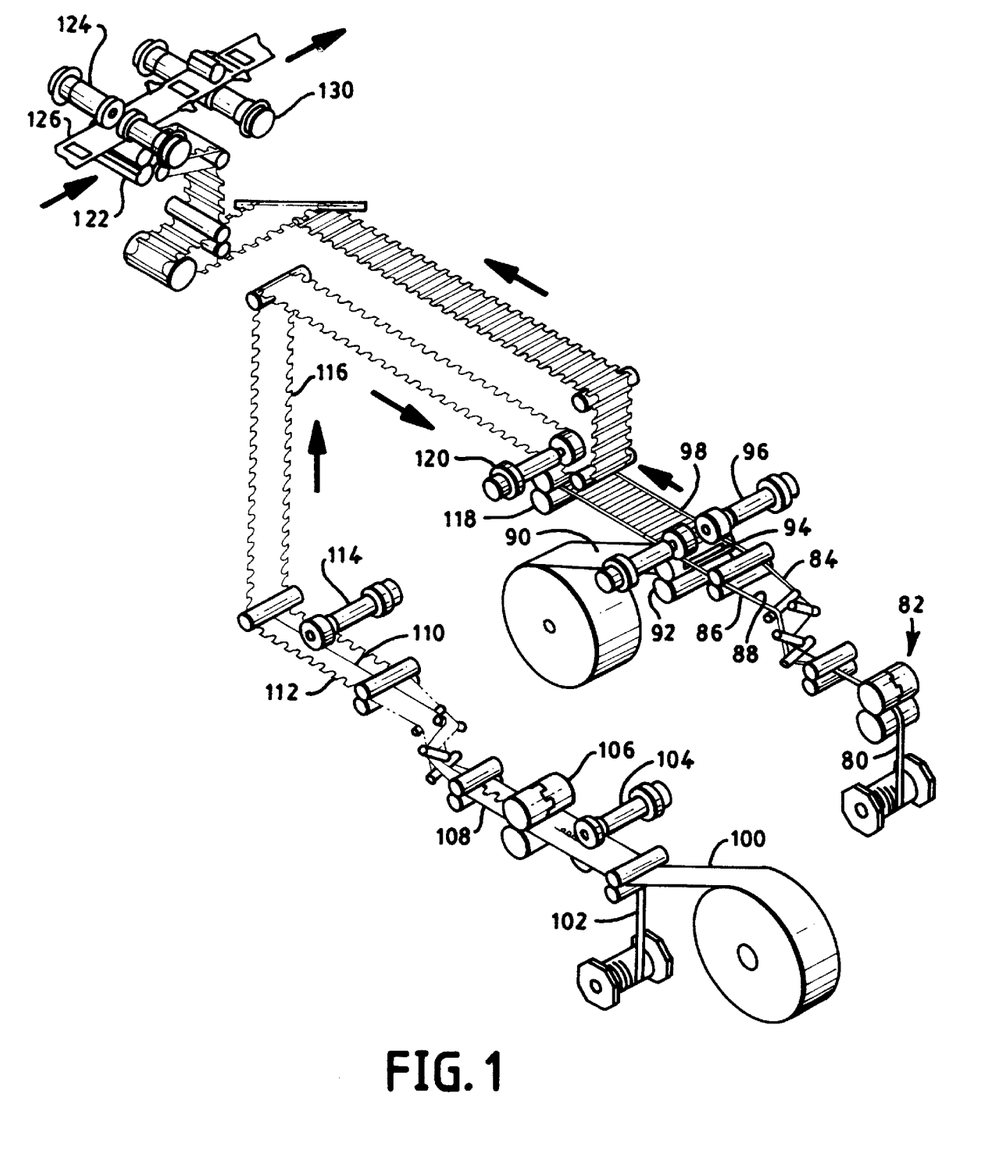
FIG. 1 representatively shows a schematic view of an example of a method of making a disposable absorbent article having a stretch band according to the present invention.
Figure 2:
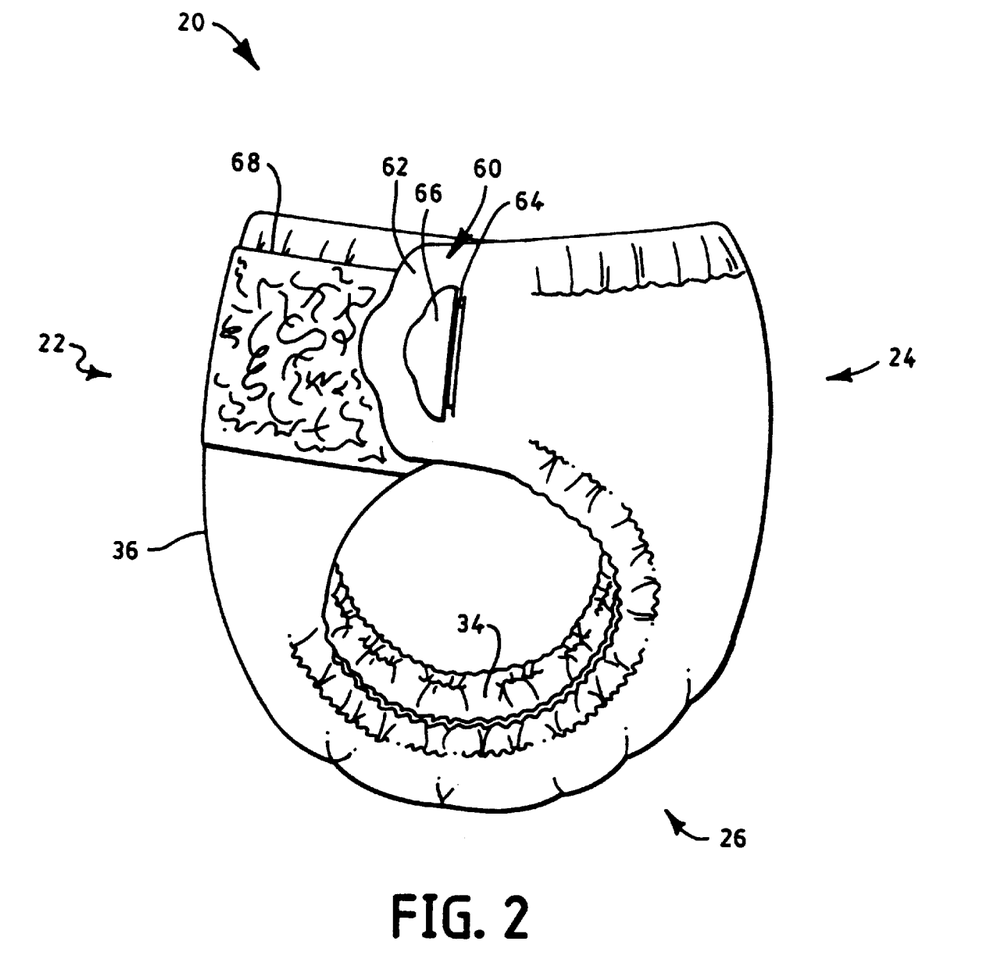
FIG. 2 representatively shows a side view of an example of a disposable absorbent article according to the present invention.
Figure 3:
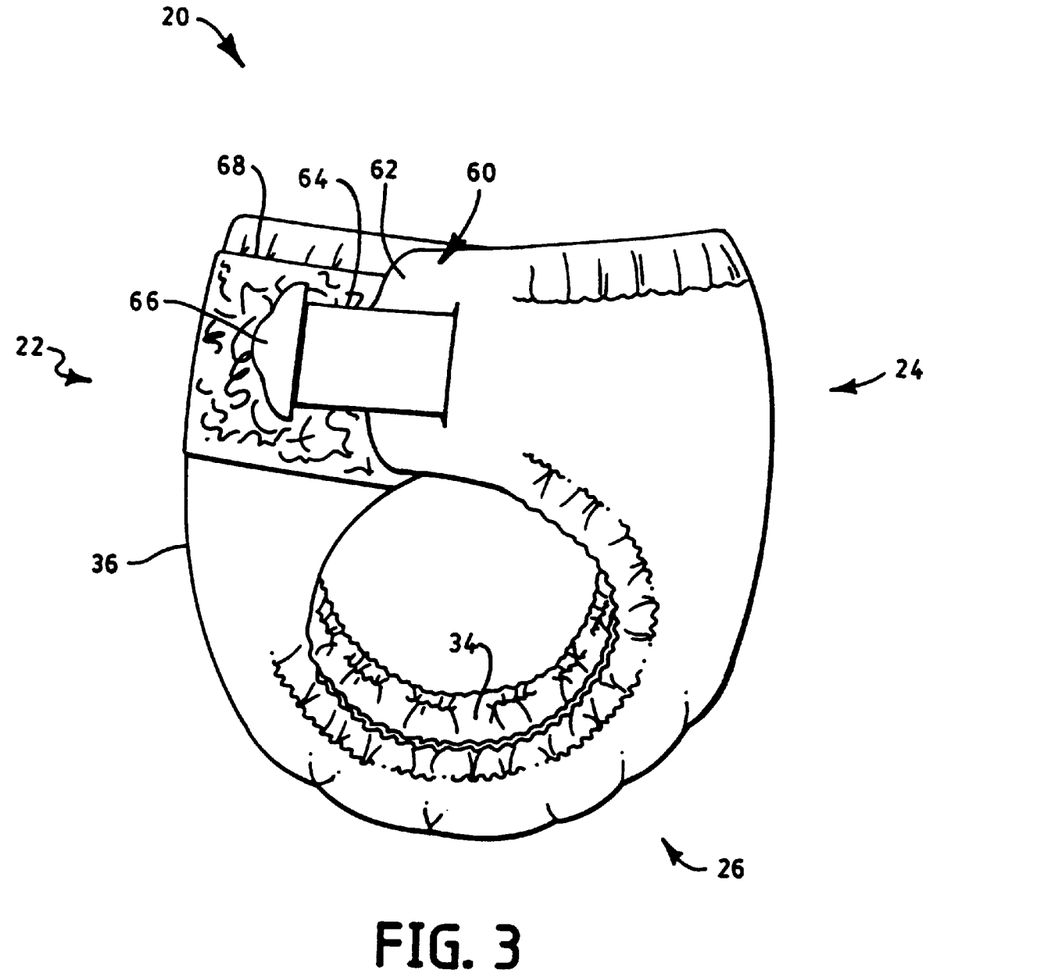
FIG. 3 representatively shows a side view of the disposable absorbent article of FIG. 2 wherein the stretch band has been extended to conform the waist regions of the article to the waist of the wearer.
Figure 4:
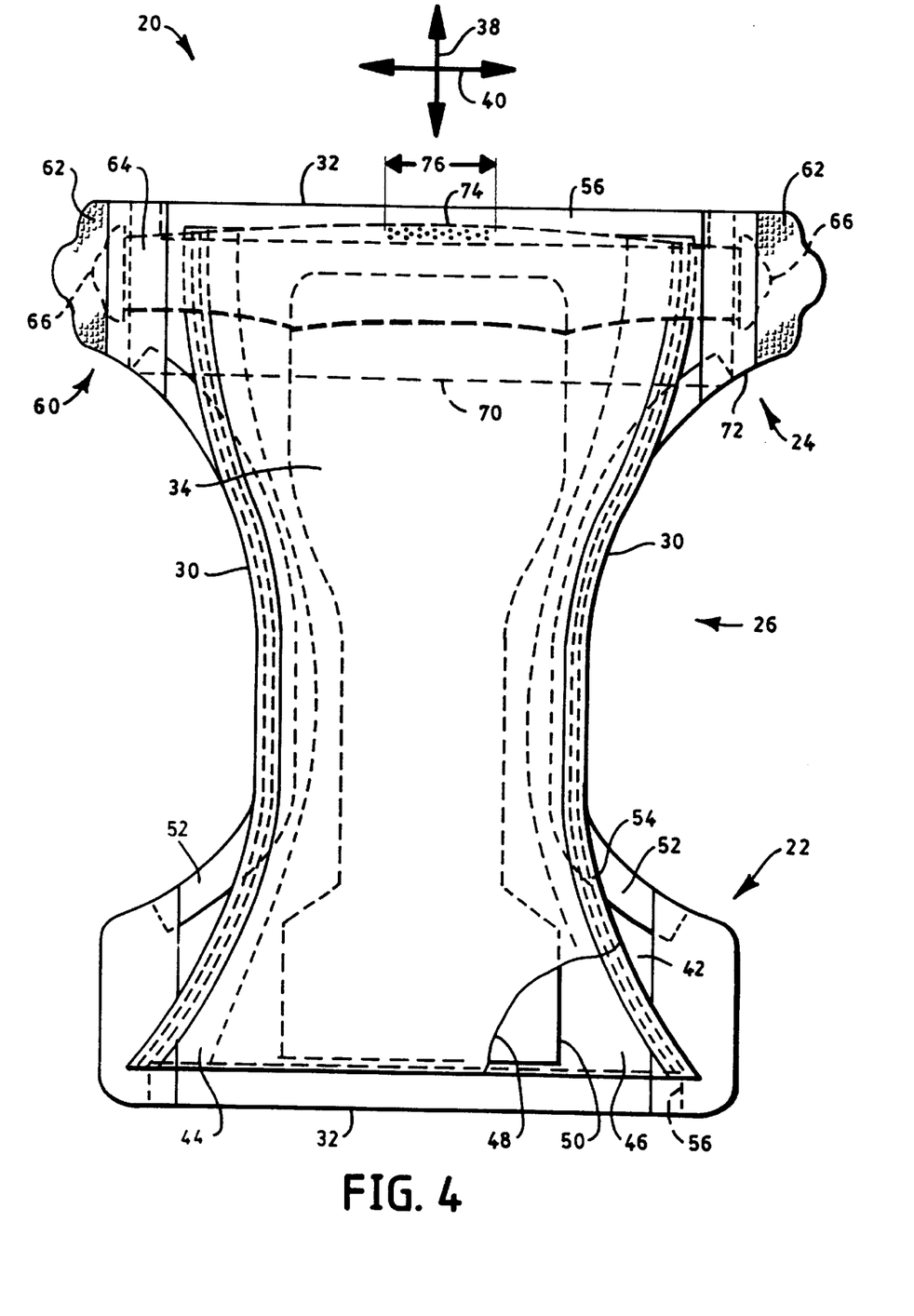
FIG. 4 representatively shows a plan view of the disposable absorbent article of FIG. 2 in an unfastened, stretched and laid flat condition with the surface of the article which contacts the wearer facing the viewer.
Figure 5:
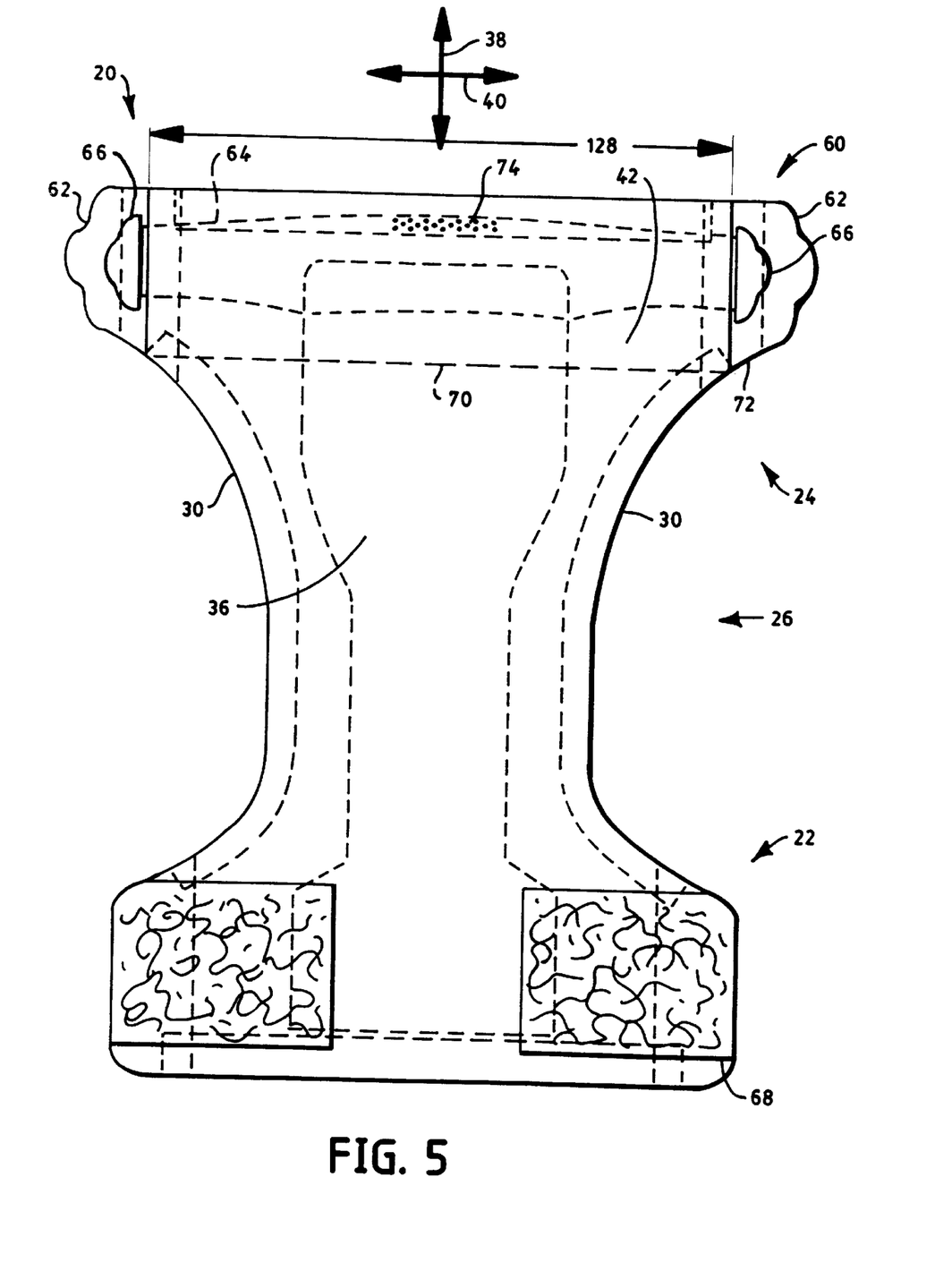
FIG. 5 representatively shows a plan view of the disposable absorbent article of FIG. 2 in an unfastened, stretched and laid flat condition with the surface of the article which contacts the wearer's clothing facing the viewer.

FIG. 1 representatively illustrates a schematic view of an example of a method of making a disposable diaper according to the present invention. FIGS. 2 and 3 representatively illustrate an example of a disposable diaper, as generally indicated at 20, which may be made according to the methods of the present invention. FIGS. 4 and 5 representatively illustrate the diaper of FIG. 2 in an unfastened, stretched and laid flat configuration. As illustrated in FIGS. 2–5, the diaper 20 defines a front waist region 22, a back waist region 24, and a crotch region 26 which extends between and connects the front and back waist regions 22 and 24. The diaper 20 further defines a pair of laterally opposed side edges 30, a pair of longitudinally opposed waist edges 32, an interior surface 34 which is configured to contact the wearer, an outer surface 36 opposite the interior surface 34, a longitudinal direction 38 and a lateral direction 40.

The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer. The laterally opposed side edges 30 of the diaper 20 generally define leg openings which may be curvilinear. The waist edges 32 of the diaper 20 are configured to encircle the waist of the wearer when worn and provide a waist opening when fastened which defines a waist perimeter dimension.

The illustrated diaper 20 includes an outer cover 42, an absorbent chassis 44 and a fastening system 60. The absorbent chassis 44 includes a backsheet 46, a bodyside liner 48 which is connected to the backsheet 46 in a superposed relation, and an absorbent core 50 which is located between the bodyside liner 48 and the backsheet 46. The fastening system 60 includes a pair of primary fasteners 62, a stretch band 64, a pair of secondary fasteners 66 attached to the laterally opposed end portions of the stretch band 64 and a waist panel 70. The stretch band 64 is slidably contained between the waist panel 70 and the outer cover 42 of the diaper 20.

The absorbent chassis 44 is configured to contain and/or absorb any body exudates discharged from the wearer. Whereas, the outer cover 42, primary fasteners 62, stretch band 64 and secondary fasteners 66 are configured to maintain the diaper 20 about the waist of the wearer, conceal the absorbent chassis 44 from view, and provide a garment-like appearance. The diaper 20 may further include leg elastics 52, containment flaps 54 and waist elastics 56 as are known to those skilled in the art. It should be recognized that individual components of the diaper 20 may be optional depending upon the intended use of the diaper 20.

A suitable arrangement for some of the different components of the diaper of the present invention is also described in U.S. patent application Ser. No. 08/907,585 entitled "A MULTI-FUNCTIONAL FASTENER FOR DISPOSABLE ABSORBENT ARTICLES" and filed Aug. 8, 1997 in the name of J. Suprise, the disclosure of which is hereby incorporated by reference.

The methods of the different aspects of the present invention are directed at reliably and consistently providing disposable absorbent articles having a stretch band 64, such as that representatively illustrated in FIGS. 2–5. A schematic view of one example of a method according to the present invention is illustrated in FIG. 1. In general, the illustrated method includes providing a continuous web of stretch band assemblies 98 each of which can include a stretch band 64 and a pair of secondary fasteners 66 attached to the laterally opposed end portions of the stretch band 64. The web of stretch band assemblies 98 is cut into discrete stretch band assemblies which are applied to a continuous web of waist panel material 116 which includes the primary fasteners 62 attached thereto. The web of waist panel material 116 is then selectively cut into individual waist panels 70 which are attached to a web of outer cover material 126 at spaced apart locations such that the stretch band 64 is slidably contained between the outer cover 42 and the waist panel 70.

Multiple absorbent chassis 44 as illustrated in FIGS. 4 and 5 are attached to the web of outer cover material 126 at spaced apart locations to provide a continuous web of interconnected diapers (not shown). In such a configuration, the front waist region 22 of the leading diaper 20 may be connected to the back waist region 24 of the trailing diaper 20 to form the continuous web of interconnected diapers. Alternatively, the back waist region 24 of the leading diaper may be connected to the front waist region 22 of the trailing diaper or the diapers may be arranged in a front-to-front/back-to-back relationship.

Additional components, such as the leg elastics 52, containment flaps 54 and waist elastics 56, may also be connected to the continuously moving web of outer cover material or the individual absorbent chassis connected thereto to provide the web of interconnected diapers. The different components of the diaper 20 may be connected together by means known to those skilled in the art such as, for example, adhesive, thermal or ultrasonic bonding. Desirably, most of the components are connected using ultrasonic bonding for improved manufacturing efficiency and reduced raw material cost.

The continuous web of stretch band assemblies 98 may be provided in a variety of manners. For example, as illustrated in FIG. 1, a continuous web of secondary fastener material 80 is unwound and passed through die cutter 82 which selectively cuts the web of secondary fastener material 80 along it's longitudinal length in the machine direction into two, laterally spaced apart ribbons of secondary fastener material 84. As used herein, the phrase "machine direction" refers to the direction in which the respective web of material is continuously moving whereas the phrase "cross machine direction" refers to the direction perpendicular to the direction in which the respective web of material is moving. The terms "longitudinal" and "lateral" also generally refer to the machine direction and cross machine direction, respectively. For example, as illustrated in FIGS. 4 and 5, the longitudinal direction 38 and lateral direction 40 of the diaper 20 correspond to the machine direction and cross machine direction, respectively, when the diapers are manufactured in an end to end or waist to waist relationship.

If it is desired to provide a nonlinear edge on the secondary fasteners, the die cutter 82 may cut the web of secondary fastener material 80 along a serpentine path thereby providing each ribbon 84 with a cut edge 86 and an opposite edge 88. In such a configuration, the discrete ribbons of secondary fastener material 84 are then crossed over one another to position the cut edge 86 of each ribbon 84 laterally outward from the opposite edge 88. As used herein, the term "outward" refers to a distance in the lateral or cross machine direction away from a longitudinal centerline of the respective moving web.

In the illustrated method, a continuous web of stretch band material 90 is also unwound and passed through slip cutter 92 which cuts the web of stretch band material 90 in the cross machine direction into individual stretch band segments 94. The opposed end portions of the discrete stretch band segments 94 are attached by bonder 96 to the spaced apart ribbons of fastener material 84 to provide a continuous web of stretch band assemblies 98. The stretch band segments 94 are attached to the ribbons of fastener material 84 at longitudinally spaced apart locations. Thus, as illustrated in FIG. 1, the web of stretch band assemblies 98 may be provided in a ladder type configuration. Desirably, at least a portion of the stretch band segments 94 includes a latent elastic material which can be activated after the diaper is assembled such that the stretch bands 94 are in a pretensioned configuration in the diaper 20. Alternatively, the stretch band segments 94 may be elongated at least about 10 percent and more desirably at least about 25 percent before being attached to the ribbons of fastener material 84 such that the stretch bands 94 are in a pretensioned configuration in the diaper 20.

As representatively illustrated in FIG. 1, the web of stretch panel assemblies 98 is then cut into discrete stretch bands by slip cutter 118. The discrete stretch bands are then attached at spaced apart locations to the continuous web of waist panel material 116 using bonder 120. The web of waist panel material 116 includes multiple pairs of primary fasteners at spaced apart locations on the laterally opposed side edges of the web 116. In the illustrated embodiment, the primary fasteners are attached to a first surface of the waist panel material 116 and the discrete stretch bands are attached to the second surface of the waist panel material 116 opposite the first surface.

The primary fasteners may be attached to the waist panel material 116 by methods known to those skilled in the art. For example, as representatively illustrated in FIG. 1, the web of waist panel material 116 may be provided by first providing a continuous web of base material 100 and attaching a ribbon of primary fastener material 102 along a longitudinal length of the web of base material 100 using bonder 104. The base material 100 is then passed through die cutter 106 which cuts the web of base material 100 and ribbon of primary fastener material 102 in the machine direction along it's longitudinal length into two continuous sections of base material 108. If it is desired to provide nonlinear edges on the primary fasteners, the die cutter 106 may cut the base material 100 and ribbon of primary fastener material 102 along a serpentine path thereby providing each section of base material 108 with a straight edge 110 and a cut edge 112. The discrete sections of base material 108 are then crossed over one another to position the cut edge 112 of each section 108 laterally outward from the straight edge 110. The straight edges 110 of each section 108 are positioned in an overlapping arrangement and bonded together by bonder 114 to provide the continuous web of waist panel material 116.

As illustrated in FIG. 1, the continuous web of waist panel material 116 with the discrete stretch bands intermittently attached thereto is selectively cut by slip cutter 122 into discrete waist panels. The discrete waist panels may then be intermittently attached by bonder 124 to the continuous web of outer cover material 126 or interconnected absorbent articles at spaced apart locations. The waist panels are attached such that the stretch band is slidably contained between the waist panels and the outer cover material or absorbent article. For example, as illustrated in FIG. 1, the outer cover material 126 having the waist panels attached thereto may be passed through capture bonder 130 which bonds the waist panels to the outer cover material 126 adjacent the stretch bands such that the stretch bands are slidably captured between the waist panel and the outer cover material 126.

Suitable bonding equipment which can be used to provide the attachment of the different components of the diaper is well known to those skilled in the art. Desirably, the bonders 96, 104, 114, 120, 124 and 130 are ultrasonic bonders for improved efficiency and cost effectiveness. For example, as illustrated in FIG. 1, the bonder 96 may include one or more rotary ultrasonic horns and an anvil roll between which the individual ends of the stretch bands and the ribbons of fastener material 84 are passed to provide the ladder type web of stretch band assemblies 98. Suitable rotary ultrasonic horns are described in U.S. Pat. No. 5,110,403 to Ehlert, the disclosure of which is hereby incorporated by reference. Such rotary ultrasonic horns generally have a diameter of from about 5 to about 20 centimeters and a width of from about 2 to about 15 centimeters. Alternatively, the ultrasonic horn may be a stationary ultrasonic horn as are also known to those skilled in the art. Other suitable ultrasonic horns and ultrasonic bonders are commercially available from Branson Sonic Power Company, a business having offices in Danbury, Conn. The bonders 96, 104, 114, 120, 124 and 130 could otherwise be a thermal or adhesive bonder as are well known.

The bonders 96, 104, 114, 120, 124 and 130 may be configured to provide the attachment of the different components in a variety of patterns and shapes or sizes. For example, the bonds may be provided as a pattern of points, dots, circles, squares, triangles and the like which may be arranged in a linear or nonlinear configuration. Such patterns may be located on the bonding horn or the anvil roll.

Suitable cutters to provide die cutters 82 and 106 and slip cutters 92, 118 and 122 to selectively cut the webs of the method of the present invention are generally known to those skilled in the art. For example, die cutter 82 may include the combination of a cutting roll and anvil roll through which the web 80 travels. The anvil roll may include a hardened steel rotating roll while the cutting roll may include one or more flexible hardened steel blades clamped on to another rotating roll. The pinching force between the blade on the cutting roll and the anvil roll creates the cut. The cutting roll may have one or more blades depending upon the desired distance between the cuts. The slip cutters 92, 118 and 122 may further be configured to provide a spacing between the individual cut pieces after they are cut. Such a spacing can be provided by transferring the cut pieces away from the cutter at a higher speed than the speed at which the web is provided to the cutter.

The continuous web of interconnected diapers provided by the above methods may further be passed through another die cutter which selectively cuts the web into discrete, individual diapers. The discrete diapers may then be folded in a conventional blade folder about a lateral fold line in the crotch region of the diaper such that the waist regions of each diaper are positioned in a facing relationship. If it is desired that the diapers be provided in a prefastened configuration, the primary fasteners may further be folded over and releasably engaged with the outer surface on the opposite waist region of each diaper. Such prefastened diapers, as illustrated in FIG. 2, may then be pulled on or off similar to conventional training pant articles.

The methods of the present invention, as representatively illustrated in FIG. 1, can reliably and consistently provide absorbent articles having a stretch band such as the diaper illustrated in FIG. 2. In particular, the use of a waist panel arrangement having the stretch band assembly attached thereto provides accurate registration and alignment to facilitate the slip cutting and high speed application of the stretch bands and fasteners to the individual diapers. Thus, the methods can provide a uniform and consistent attachment of each stretch band to the diaper. The methods can further result in reduced waste through the use of serpentine cutting on nested pattern webs, such as the webs of waist panel material and stretch band material with the fastener material attached thereto, and the crossing over of the serpentine cut webs to provide shaped end portions on the stretch bands and waist panels.

The different components of the absorbent articles made by the methods described above may include a variety of materials. For example, as representatively illustrated in FIGS. 2–5, the outer cover 42 of the diaper 20 may suitably be composed of a material which is either liquid permeable or liquid impermeable. Since the absorbent chassis 44 of the different aspects of the present invention is designed to contain the body exudates discharged from the wearer, it is generally not necessary that the outer cover 42 be liquid impermeable. For example, the outer cover 42 may include various woven or nonwoven materials such as spunbond material, meltblown material, cotton material, rayon material or combinations thereof such as a spunbond-meltblown-spunbond (SMS) laminate material. The outer cover 42 may otherwise be at least partially liquid impermeable to further prevent any leakage of body exudates. For example, a typical outer cover 42 can be manufactured from a thin plastic film or other flexible liquid-impermeable material, woven or nonwoven fibrous layers, microporous "breathable" materials, elastic materials and combinations thereof.

The absorbent chassis 44 of the diaper 20 is suitably connected to the outer cover 42 to provide the disposable diaper 20. The absorbent chassis 44 may be connected to the outer cover 42 in manners well known to those skilled in the art. For example, the absorbent chassis 44 may be bonded to the outer cover 42 using adhesive, thermal or ultrasonic bonding techniques known to those skilled in the art. Alternatively, the absorbent chassis 44 may be connected to the outer cover 42 using conventional fasteners such as buttons, hook and loop type fasteners, adhesive tape fasteners, and the like. The other components of the diaper 20 may be suitably connected together using similar means.

Desirably, the absorbent chassis 44 is connected to the outer cover 42 only at or adjacent the waist edges 32 of the outer cover 42 thereby creating a front attached portion, a back attached portion and an unattached portion which extends between and connects the attached portions. The unattached portion of the absorbent chassis 44 remains substantially unattached to the outer cover 42 and is generally configured to fit between the legs of the wearer and at least partially cover the lower torso of the wearer when in use. As a result, the unattached portion is generally the portion of the absorbent chassis 44 which is configured to initially receive the body exudates from the wearer. Thus, the absorbent chassis 44 is connected to the outer cover 42 in such a manner to secure the chassis 44 in place while not adversely restricting the movement of the outer cover 42 in use. Alternatively, the absorbent chassis 44 may be attached to the outer cover 42 along the entire longitudinal length of the absorbent chassis 44 or any portion thereof or along only the outer periphery of the absorbent chassis 44.

As representatively illustrated in FIG. 4, the absorbent chassis 44 according to the present invention may include a backsheet 46, a bodyside liner 48 which is connected to the backsheet 46 in a superposed relation, and an absorbent core 50 which is located between the bodyside liner 48 and the backsheet 46. In alternative configurations wherein the outer cover 42 is at least partially resistant to the flow of liquids therethrough, the backsheet 46 may optionally be omitted from the absorbent chassis 44.

The absorbent chassis 44 is generally conformable and capable of absorbing and retaining body exudates. The absorbent chassis 44 may have any of a number of shapes and sizes. For example, as representatively illustrated in FIG. 4, the absorbent chassis 44 may be rectangular, I-shaped or T-shaped. The size and absorbent capacity of the absorbent chassis 44 should be compatible with the size of the intended wearer and the fluid loading imparted by the intended use of the diaper 20. Typically, it is desirable that the absorbent chassis 44 have an absorbent capacity of at least about 300 grams of urine. It is generally preferred that the absorbent chassis 44 be narrower in the crotch region 26 than in the waist regions 22 and 24. It has been found that the absorbent chassis 44 of the present invention is particularly useful when the width dimension in the crotch region 26 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension of the absorbent chassis 44 allows the absorbent chassis 44 to better fit between the legs of the wearer.

The bodyside liner 48 of the absorbent chassis 44, as representatively illustrated in FIG. 4, suitably presents a bodyfacing surface which is intended to be worn adjacent the body of the wearer and is compliant, soft feeling and nonirritating to the wearer's skin. Further, the bodyside liner 48 may be less hydrophilic than the absorbent core 50, to present a relatively dry surface to the wearer, and may be sufficiently porous to be liquid permeable, permitting liquid to readily penetrate through its thickness. A suitable bodyside liner 48 may be manufactured from a wide selection of web materials, such as woven and nonwoven fabrics, porous foams, reticulated foams, apertured plastic films, natural fibers (for example, wood or cotton fibers), synthetic fibers (for example, polyester or polypropylene fibers), or a combination of natural and synthetic fibers. The bodyside liner 48 is suitably employed to help isolate the wearer's skin from fluids held in the absorbent core 50 of the absorbent chassis 44.

The backsheet 46 of the absorbent chassis 44, as representatively illustrated in FIG. 4, may suitably be composed of a material which is either liquid permeable or liquid impermeable. It is generally preferred that the backsheet 46 be formed from a material which is substantially impermeable to fluids. A typical backsheet can be manufactured from a thin plastic film or other flexible liquid-impermeable material. The backsheet 46 may also be constructed of a material which is similar to the material described as being suitable for the outer cover 42.

The bodyside liner 48 and backsheet 46 are generally adhered to one another so as to form a pocket in which the absorbent core 50 is located to provide the absorbent chassis 44. The bodyside liner 48 and backsheet 46 may be adhered directly to each other around the outer periphery of the absorbent chassis 44 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 48 to the backsheet 46. It should be noted that both the bodyside liner 48 and the backsheet 46 need not extend completely to the outer periphery of the absorbent chassis 44. For example, the backsheet 46 may extend to the outer periphery of the absorbent chassis 44 while the bodyside liner 48 may be attached to the backsheet 46 inboard of the outer periphery of the absorbent chassis 44, or more towards the longitudinal centerline of the diaper 20. In alternative configurations, especially wherein the backsheet 46 is omitted, the bodyside liner 48 may be suitably adhered directly to the absorbent core 50 or to the outer cover 42.

The absorbent core 50, as representatively illustrated in FIG. 4, is positioned between the bodyside liner 48 and the backsheet 46 to form the absorbent chassis 44. The absorbent core 50 is desirably conformable and capable of absorbing and retaining body exudates. The absorbent core 50 may have any of a number of shapes and sizes. For example, the absorbent core may be rectangular, I-shaped or T-shaped. It is generally preferred that the absorbent core 50 be narrower in the crotch region 26. The size of the absorbent core 50 should be compatible with the size of the intended wearer and the desired absorbent capacity of the absorbent chassis 44.

The absorbent core 50 of the absorbent chassis 44 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 50 may also comprise selected blends of the various types of fibers mentioned above.

In a particular aspect of the invention, the absorbent core 50 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 50 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 50 may comprise a laminate of fibrous webs and high-absorbency material or other suitable means of maintaining a high-absorbency material in a localized area.

As representatively illustrated in FIG. 4, the absorbent chassis 44 of the disposable diaper 20 may include a pair of containment flaps 54 which are configured to provide a barrier to the lateral flow of body exudates. The containment flaps 54 may be located along the laterally opposed side edges of the absorbent chassis 44. Each containment flap 54 typically defines an unattached edge which is configured to maintain an upright, perpendicular configuration in at least the crotch region 26 of the diaper 20 to form a seal against the wearer's body. The containment flaps 54 may extend longitudinally along the entire length of the absorbent chassis 44 or may only extend partially along the length of the absorbent chassis 44. When the containment flaps 54 are shorter in length than the absorbent chassis 44, the containment flaps 54 can be selectively positioned anywhere along the side edges of the absorbent chassis 44. In a particular aspect of the invention, the containment flaps 54 extend along the entire length of the absorbent chassis 44 to better contain the body exudates.

Such containment flaps 54 are generally well known to those skilled in the art. For example, suitable constructions and arrangements for containment flaps 54 are described in U.S. Pat. No. 4,704,116 issued Nov. 3, 1987, to K. Enloe the disclosure of which is hereby incorporated by reference.

The disposable diaper 20 of the different aspects of the present invention may further include elastics at the waist edges 32 and side edges 30 of the diaper 20 to further prevent the leakage of body exudates and support the absorbent chassis 44. For example, as representatively illustrated in FIG. 4, the diaper 20 of the present invention may include a pair of leg elastic members 52 which are connected to the laterally opposed side edges 30 in the crotch region 26 of the diaper 20 and a pair of waist elastic members 56 which are connected to the longitudinally opposed waist edges 32 of the diaper 20. The leg elastics 52 and waist elastics 56 are generally adapted to fit about the legs and waist of a wearer in use to maintain a positive, contacting relationship with the wearer to effectively reduce or eliminate the leakage of body exudates from the diaper 20.

Materials suitable for use as the leg elastics 52 and waist elastics 56 are well known to those skilled in the art.

Exemplary of such materials are sheets or strands or ribbons of a polymeric, elastomeric material which are adhered to the outer cover 42 in a stretched position, or which are attached to the outer cover 42 while the outer cover is pleated, such that elastic constrictive forces are imparted to the outer cover 42. The leg elastics may also include such materials as polyurethane, synthetic and natural rubber.

The absorbent article of the different aspects of the present invention further includes a multi-functional fastening system 60 for securing the absorbent article about the waist of the wearer. The multi-functional fastening system includes fasteners located on one of the waist regions 22 and 24 of the diaper 20 which are configured to releasably engage the opposite waist region of the diaper 20 to maintain the diaper about the waist of the wearer. The use of fasteners which are refastenable or releasably engageable allows for ease of securing and removing the diaper 20 from the waist of the wearer.

As representatively illustrated in FIGS. 2–5, the multi-functional fastening system 60 of the present invention includes a pair of primary fasteners 62 which are located on the side edges 30 of the diaper 20 in the back waist region 24 of the diaper 20. In such a configuration, the primary fasteners 62 are configured to encircle the hips of the wearer and engage the outer surface 36 of the front waist region 22 of the diaper 20 to maintain the diaper 20 on the wearer. Alternatively, the primary fasteners 62 may be located on the front waist region 22 and may be configured to releasably engage the outer surface 36 of the back waist region 24 of the diaper 20.

Desirably, the primary fasteners 62 are releasably engageable directly with the outer surface of the outer cover 42 of the diaper 20 to provide improved ease of fastening. Alternatively, as representatively illustrated in FIGS. 2–5, the disposable diaper 20 of the present invention may further include an attachment panel 68 located on the outer cover 42 in one of the waist regions 22 and 24 of the diaper 20. In such a configuration, the primary fasteners 62 are releasably engageable with the attachment panel 68 to maintain the diaper 20 about the waist of the wearer. When the primary fasteners 62 are releasably engaged, the side edges 30 of the diaper 20 define leg openings which are configured to encircle the legs of the wearer and the waist edges 32 define a waist opening which is configured to encircle the waist of the wearer. As illustrated in FIG. 5, the attachment panel 68 may include two separate panels located along the opposite side edges in one of the waist regions 22 and 24 of the diaper 20. Alternatively, the attachment panel 68 may include a single piece of material which extends substantially across the respective waist edge 32 of the diaper 20.

In a particular embodiment, the primary fasteners 62 are configured to be releasably engaged with the outer surface of the opposite waist region 22 and 24 of the diaper 20 before the diaper 20 is placed on the wearer to provide a prefastened diaper. In such a configuration, the prefastened diaper 20 can be pulled on or off over the legs and hips of the wearer. If the diaper 20 becomes soiled during use, the primary fasteners 62 can be disengaged to easily remove the diaper 20 from the waist of the wearer with reduced risk of undesirably soiling the clothes or legs of the wearer. Thus, in such a configuration, the diaper 20 of the different aspects of the present invention can be configured to be pulled on or off over the hips of the wearer such as conventional training pants and can be applied to or removed by engaging or disengaging the fasteners similar to conventional diaper articles.

The multi-functional fastening system 60 on the disposable diaper 20 of the present invention further includes a stretch band having a pair of secondary fasteners thereon to provide improved securement of the diaper 20 about the waist of the wearer after the primary fasteners 62 have been releasably engaged. The stretch band and secondary fasteners of the present invention are configured to further conform the waist regions 22 and 24 of the diaper 20 to the waist of the wearer. For example, as representatively illustrated in FIGS. 2–5, the diaper 20 may include a stretch band 64 which includes a pair of secondary fasteners 66 located on the opposed end portions of the stretch band 64.

The stretch band 64 and secondary fasteners 66 are located in one of the waist regions 22 and 24 of the diaper 20 and are configured to encircle the hips of the wearer and engage the outer surface 36 in the opposite waist region 22 and 24 of the diaper 20. For example, the stretch band 64 and secondary fasteners 66 may be located along the waist edge 32 of the diaper 20 in the back waist region 24 of the diaper 20. In such a configuration, the stretch band 64 and secondary fasteners 66 are configured to encircle the back waist region 24 and hips of the wearer and engage the outer surface 36 of the front waist region 22 of the diaper 20 to maintain the diaper 20 on the wearer. Alternatively, the stretch band 64 and secondary fasteners 66 may be located on the front waist region 22 and may be configured to releasably engage the outer surface 36 of the back waist region 24 of the diaper 20.

Desirably, the secondary fasteners 66 are releasably engageable directly with the outer surface of the outer cover 42 of the diaper 20 to provide improved ease of fastening. Alternatively, as described above and representatively illustrated in FIG. 5, the diaper 20 of the present invention may further include an attachment panel 68 located on the outer cover 42 in one of the waist regions 22 and 24 of the diaper 20. In such a configuration, the secondary fasteners 66 may also be releasably engageable with the attachment panel 68 to maintain the diaper 20 about the waist of the wearer.

The use of such a stretch band 64 with secondary fasteners 66 has been found to be particularly desirable when the primary fasteners 62 are releasably engaged with the respective waist region of the diaper 20 to provide a prefastened diaper which can be pulled on over the legs and hips of the wearer. In such a configuration, the waist opening of the diaper 20 when the primary fasteners 62 are engaged must be sufficient to allow the prefastened diaper to be pulled over the hips of the wearer. However, the circumference of the waist of the wearer is typically less than the circumference around the hips of the wearer. Thus, the waist opening of the prefastened diaper may not conform to the waist of the wearer which may undesirably result in leaks. In such a configuration, the stretch band 64 and secondary fasteners 66 of the diaper 20 of the present invention are configured to conform the waist regions of the diaper 20 to the wearer after the prefastened diaper is pulled on the wearer. Thus, the care giver is not required to reposition the primary fasteners 62 to conform the waist regions 22 and 24 to the waist of the wearer. As a result, when the diaper 20 is to be removed from the wearer, the care giver may simply disengage the secondary fasteners 66 if necessary and pull the prefastened diaper down over the hips and legs of the wearer without having to reposition the primary fasteners 62.

In such configurations, the stretch band 64 and secondary fasteners 66 are intended to maintain the diaper 20 in a close conforming fit about the waist of the wearer to reduce the leakage of body exudates when in use. The primary fasteners 62 are intended to maintain the front and back waist regions 22 and 24 of the diaper 20 connected in such a manner that the diaper 20 can be pulled on or off over the hips of the wearer after the secondary fasteners 66 have been disengaged. The secondary fasteners 66 may also be selectively disengaged to facilitate inspection of the diaper 20 to determine if it has been soiled. The primary fasteners 62 can also provide a "childproofing function" by maintaining the diaper 20 at least partially secured about the waist of the wearer if the wearer disengages the secondary fasteners 66.

Suitable fasteners are well known to those skilled in the art and can include adhesive tape tab fasteners, hook and loop fasteners, mushroom fasteners, snaps, pins, bands and the like, and combinations thereof. For example, as representatively illustrated in FIGS. 2–5, the primary fasteners 62 and secondary fasteners 66 may be hook type fasteners and the outer cover 42 or attachment panel 68 may be configured to function as a complimentary loop type fastener. Desirably, the fasteners 62 and 66 are hook type fasteners which are releasably engageable with the outer cover 42. Such an arrangement provides the ability to vary the size of the waist opening in very small increments over a wide range to fit the waist of the wearer. The fasteners may have any shape and size which provides the desired fastening of the diaper 20 about the waist of the wearer. It is further desirable that the outer surface of the secondary fasteners 66 provide a visual cue to the care giver as to their location. For example, in one embodiment, the secondary fasteners 66 are of a different color than the outer surface of the diaper 20 to enable the care giver to easily determine the location of the secondary fasteners 66.

Materials suitable for use as the stretch band 64 of the different aspects of the present invention may be similar to those materials described above as being suitable for the outer cover 42. Desirably, the stretch band 64 is made of an elastic material which is capable of elongating at least about 50 percent and more desirably at least about 100 percent to provide improved fit about the waist of the wearer. For example, the stretch band 64 may comprise a neck bonded laminate material which includes a KRATON film material commercially available from the Dow Chemical Company, a business having offices located in Midland, Mich. Alternatively, the stretch band 64 may include portions which include elastic material and portions which include inelastic material.

Desirably, the stretch band 64 is made of a latent elastic material which can be activated after the diaper 20 is manufactured. The use of such a latent elastic material eliminates the need to maintain the stretch band 64 in a tensioned condition as the diaper is manufactured. Suitable latent elastic materials are known to those skilled in the art. For example, suitable latent elastic materials are commercially available from Exxon under the trade designation EXX601. Alternative latent elastic materials are described in U.S. patent application Ser. No. 08/854,934 filed May 13, 1997 and entitled "IMPROVED COMPOSITE ELASTIC MATERIAL AND PROCESS FOR PRODUCING THE SAME", the disclosure of which is hereby incorporated by reference. The latent elastic material may be activated by a variety of methods known to those skilled in the art. For example, the latent elastic stretch bands may be activated by heating the diaper after it is manufactured to cause the material to retract.

The primary fasteners 62, stretch band 64 and secondary fasteners 66 may be incorporated into the diaper 20 of the different aspects of the present invention in a variety of different manners known to those skilled in the art. For example, in the illustrated embodiments and as described above, the diaper 20 may further include a waist panel 70 which defines a first surface, a second surface opposite the first surface and a pair of laterally opposed side margins 72. The primary fasteners 62 are attached to the first surface of the waist panel 70 along the side margins 72 and the stretch band 64 and secondary fasteners 66 are attached to the second surface of the waist panel 70. In such a configuration, the waist panel 70 can be located in the diaper 20 between the outer cover 42 and absorbent chassis 44 in one of the waist regions 22 and 24 and the stretch band 64 can be slidably contained between the waist panel 70 and the outer cover 42.

The primary fasteners 62 may be adhered to the side margins 72 on the first surface of the waist panel 70 by any means known to those skilled in the art such as adhesive bonds, sonic bonds or thermal bonds. The secondary fasteners 66 may also be suitably connected to the end portions of the stretch band 64 using similar means. The stretch bands 64 with the secondary fasteners 66 are desirably attached to the second surface of the waist panel 70 by releasably engaging the secondary fasteners 66 with the second surface of the waist panel 70.

To provide the improved fit about the waist of the wearer without adversely affecting the appearance of the outer cover 42 of the diaper 20, the majority of the length of the stretch band 64 desirably is positioned behind the outer cover 42 as illustrated in FIGS. 2–5. In such a configuration, the outer cover 42 defines a width in the lateral direction 40 which is less than a width of the waist panel 70 in the lateral direction such that the end portions of the stretch band 64 and the secondary fasteners extend laterally beyond the side edge of the outer cover 42. Thus, the width of the outer cover 42 should be less than the distance between the secondary fasteners 66 of the stretch band 64 on waist panel 70 but sufficient to hide the majority of the stretch band 64 between the secondary fasteners 66 before the stretch band 64 has been extended to provide the improved fastening. For example, as illustrated in FIG. 5, the outer cover 42 defines a width 128 at the respective waist region where the stretch band 64 is located which is less than the distance between the secondary fasteners 66. Desirably, the width 128 of the outer cover 42 at this location is from about 75 to about 99 percent of the distance between the secondary fasteners 66 when secured to the waist panel 70 before being extended for improved functionality and aesthetics.

As a result, the outer cover 42 and waist panel 70 are configured to function as a single sleeve through which the stretch band 64 is slidably contained. Thus, the end portions of the stretch band 64 and the secondary fasteners 66 are located on the outer surface 36 of the diaper and the remaining portion of the stretch band 64 extends through to and along the interior surface of the outer cover 42 between the outer cover 42 and the waist panel 70. Alternatively, the stretch band 64 may extend behind the outer cover 42 and be located between the outer cover 42 and absorbent chassis 44, between any of the layers of the absorbent chassis 44 or between the absorbent chassis 44 and the wearer. As illustrated, the secondary fasteners 66 are desirably configured to releasably engage the outer surface of the waist panel 70 between the side edges of the outer cover 42 and the primary fasteners 62 for improved control and ease of fastening.

A portion of the stretch band 64 between the side edges of the outer cover 42 may be secured to the other portions of the diaper 20 such as the interior surface of the outer cover 42 or the outer surface of the waist panel 70 to provide an attached portion 74 as illustrated in FIG. 4. The attached portion 74 of the stretch band 64 may be secured using methods known to those skilled in the art such as adhesive, sonic or thermal bonding. Desirably, the attached portion 74 defines an attached length 76 as illustrated in FIG. 4 which is less than about 75 percent and more desirably less than about 50 percent of the total length of the stretch band 64. Such an attached length provides sufficient securement of the stretch band to the diaper 20 without adversely affecting the ability of the stretch band to conform to the waist of the wearer to provide the improved fit.

The stretch band 64 may define any length and width which provide the desired improved fastening and fit about the wearer. For example, the stretch band 64 may define a length which is from about 7 to about 35 centimeters and a width which is from about 1 to about 10 centimeters. Desirably, the stretch band 64 defines a length which is slightly less than the width of the diaper 20 at the respective waist region such that the stretch band 64 is slightly elongated to pretension the waist region.

The waist panel 70 may suitably be attached to the other portions of the diaper 20 using attachment methods described herein. For example, the waist panel 70 may be ultrasonically bonded to the outer cover 42. In a particular embodiment wherein the stretch band 64 is slidably contained between the waist panel 70 and the outer cover 42, the second surface of the waist panel 70 is attached to the inner surface of the outer cover 42 adjacent and along the stretch band 64 to provide a sleeve through which the stretch band is slidably contained.

Materials suitable for use as the waist panel 70 of the different aspects of the present invention are similar to those materials described above as being suitable for the outer cover 42. Desirably, the waist panel 70 is made of a nonwoven material. For example, the waist panel 70 may comprise a spunbond material which includes polypropylene. Alternatively, the waist panel 70 may include a stretchable material.

If it is desired that the absorbent article of the present invention be prefastened, the absorbent article of the present invention may further include a pair of releasable side bonds (not shown) for improved reliability of maintaining the article in the prefastened condition particularly when it is being pulled on or off over the hips of the wearer. Absorbent articles including such releasable side bonds are further described in U.S. Patent Application entitled "DISPOSABLE ABSORBENT ARTICLES HAVING PASSIVE SIDE BONDS AND ADJUSTABLE FASTENING SYSTEMS" filed in the name of Elsberg on the same date as the instant application and given Attorney Docket Number 13,611, the disclosure of which is hereby incorporated by reference. For example, the diaper 20 may include a pair of releasable side bonds which releasably connect the side edges 30 of the diaper in the front and back waist regions 22 and 24 of the diaper 20. In such a configuration, the releasable side bonds can assist the fastening system 60 in maintaining the diaper 20 in a prefastened condition as the diaper 20 is pulled up or down over the hips of the wearer. Moreover, the releasable side bonds can prevent movement and shifting of the waist regions 22 and 24 relative to each other for improved fit and performance. The releasable side bonds can also prevent rollover or folding of the side edges 30 and waist edges 32 of the diaper 20 as it is pulled over the wearers hips.

The different aspects of the present invention advantageously provide disposable absorbent articles having a fastening system which includes a stretch band and methods of making the same. The fastening system may be prefastened to releasably engage the front and back waist portions to allow the absorbent article to be pulled up or down over the hips of the wearer such as conventional training pants. Moreover, the stretch band of the fastening system can be used to further conform the front and back waist portions of the absorbent article to maintain the absorbent article about the waist of the wearer after the article has been placed on the wearer.

As a result, the absorbent article of the present invention is designed to conform to the waist and body of the wearer to effectively contain bodily exudates while still being capable of being reliably pulled up or down over the hips of the wearer to assist in the toilet training of the wearer. Moreover, similar to conventional diapers, the absorbent article of the present invention can advantageously be applied to and removed from the wearer with relative ease and cleanliness.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A method of making a prefastened disposable absorbent article which defines a front waist region, a back waist region, a crotch region which extends between and connects said waist regions, a pair of opposed side edges and a pair of opposed waist edges, said method comprising the steps of:
   a) providing a waist panel which defines a first surface, a second surface and a pair of opposed side margins and which includes a pair of primary fasteners attached to said first surface on said opposed side margins;
   b) attaching a stretch band to said second surface of said waist panel wherein said stretch band includes a pair of secondary fasteners on opposite end portions of said stretch band which are releasably engaged with said second surface of said waist panel;
   c) attaching said second surface of said waist panel to an outer cover of said absorbent article in said back waist region of said absorbent article wherein said outer cover defines a width which is less than a distance between said secondary fasteners on said stretch band and wherein said stretch band is slidably contained between said outer cover and said waist panel;
   d) attaching an absorbent chassis to said outer cover to provide said disposable absorbent article;
   e) folding said disposable absorbent article about a fold line extending in a lateral direction through said crotch region of said absorbent article thereby positioning said waist regions of said absorbent article in a facing relationship; and
   f) releasably engaging said primary fasteners with an outer surface of said absorbent article in said front waist region of said absorbent article to provide said prefastened absorbent article wherein said secondary fasteners on said stretch band are configured to releasably engage said front waist region to conform said waist regions to a wearer's body after said prefastened absorbent article is pulled on over a wearer's hips.

2. The method of claim 1 wherein said primary fasteners and said secondary fasteners are hook material of a hook and loop type fastener.

3. The method of claim 1 wherein said stretch band includes a latent elastic material and said method further comprises activating said stretch band to pretension said stretch band.

4. The method of claim 1 wherein said stretch band is provided by a process comprising:
   a) providing two continuous, laterally spaced apart ribbons of secondary fastener material;
   b) attaching band segments between and to said ribbons of fastener material at longitudinally spaced apart locations in a continuous ladder type configuration to provide a continuous web of said stretch bands; and
   c) selectively cutting said continuous web of stretch bands to provide said stretch band having said secondary fasteners on said end portions.

5. The method of claim 4 wherein said band segments are attached to said ribbons of secondary fastener material using ultrasonic bonding.

6. The method of claim 4 and further comprising elongating said band segments at least about 25 percent before attaching said band segments to said ribbons of fastener material.

7. The method of claim 4 wherein said step of attaching said stretch band to said waist panel includes attaching a portion of said band segment of said stretch band to said second surface of said waist panel.

8. The method of claim 7 wherein said attached portion of said band segment defines an attached length which is less than about 75 percent of a total length of said band segment.

* * * * *